(12) United States Patent
Matsumoto et al.

(10) Patent No.: US 6,733,643 B2
(45) Date of Patent: May 11, 2004

(54) APPARATUS FOR MEASURING A COMPONENT IN A LIQUID SAMPLE

(75) Inventors: Toru Matsumoto, Tokyo (JP); Toru Murakami, Tokyo (JP)

(73) Assignee: NEC Corporation, Tokyo (JP)

( * ) Notice: Subject to any disclaimer, the term of this patent is extended or adjusted under 35 U.S.C. 154(b) by 167 days.

(21) Appl. No.: 09/916,514

(22) Filed: Jul. 30, 2001

(65) Prior Publication Data

US 2002/0014409 A1 Feb. 7, 2002

(30) Foreign Application Priority Data

Aug. 1, 2000 (JP) ........................................ 2000-233390

(51) Int. Cl.[7] ............................................. G01N 27/327
(52) U.S. Cl. ............................. 204/403.14; 204/403.01; 204/400; 204/408; 422/61
(58) Field of Search ................................. 204/401, 402, 204/400, 403.01, 403.14, 416, 408; 422/55, 58, 61

(56) References Cited

U.S. PATENT DOCUMENTS 5,096,669 A * 3/1992 Lauks et al. ........... 204/403.02
5,520,787 A * 5/1996 Hanagan et al. ....... 204/403.14

FOREIGN PATENT DOCUMENTS

| JP | 62-11160 | 1/1987 |
|---|---|---|
| JP | 63-1971 | 1/1988 |
| JP | 2-54027 | 2/1990 |
| JP | 2-54028 | 2/1990 |

* cited by examiner

Primary Examiner—Alex Noguerda
(74) Attorney, Agent, or Firm—McGinn & Gibb, PLLC

(57) ABSTRACT

A measurement apparatus, including a biosensor for carrying out measurement of a specified component in a liquid sample using an enzymatic reaction, a computation processing part for obtaining the computed value by computing an output signal of the biosensor, and a container for storing a calibration liquid for calibrating the biosensor, equipped with temperature control means (a heater 40, a thermostat 41) for keeping the calibration liquid at a constant temperature, saves an installation space by miniaturizing an apparatus, suppresses the running cost, and improves the measurement precision.

8 Claims, 14 Drawing Sheets

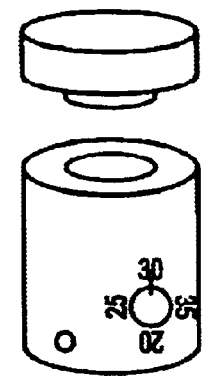
FIG.1A    FIG.1B
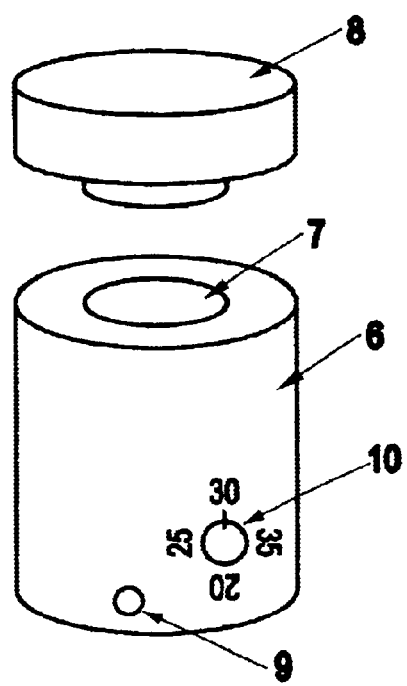
FIG.2

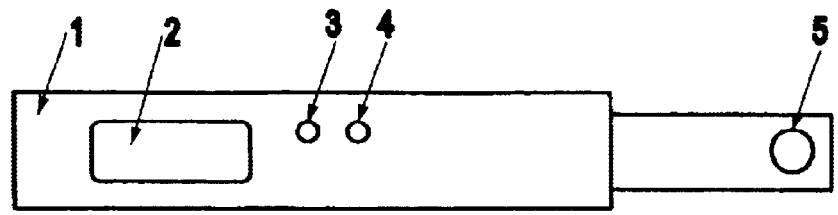
FIG.3
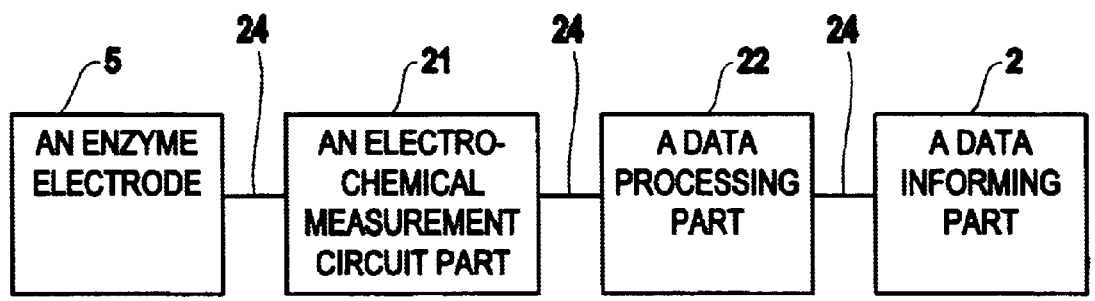
FIG.4
 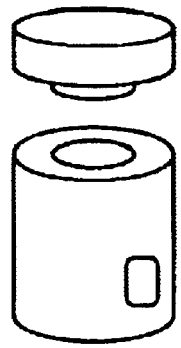
FIG.5A  FIG.5B

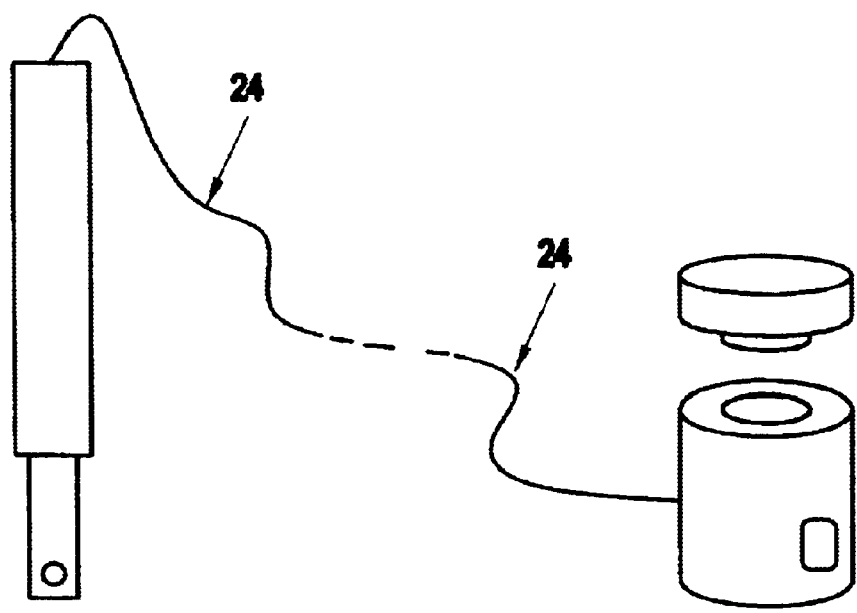
FIG.11A   FIG.11B
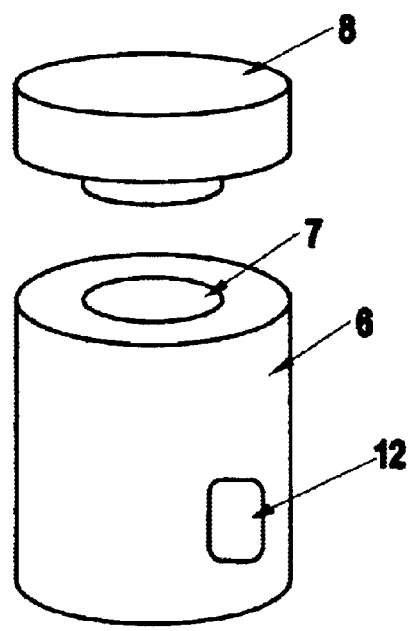
FIG.12

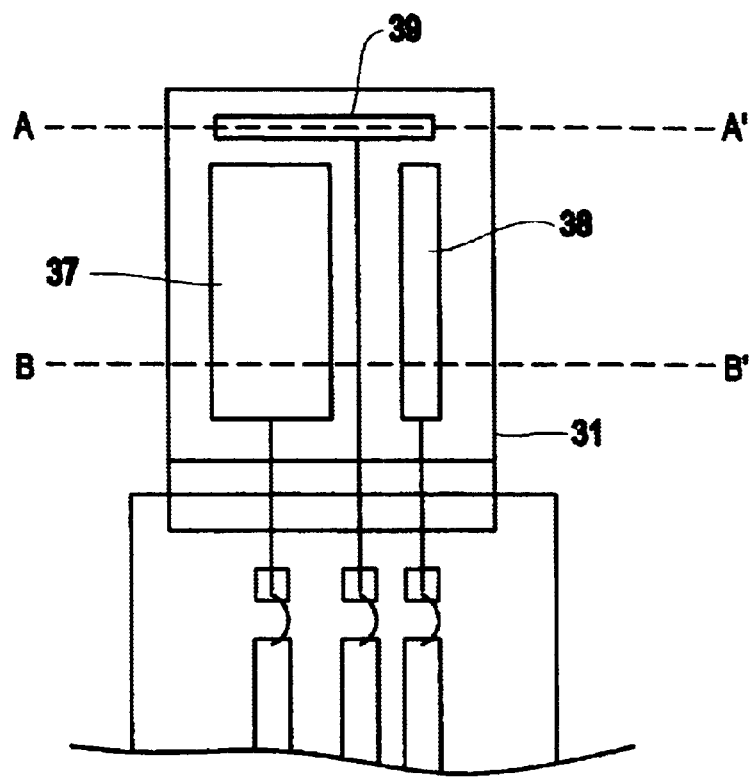
FIG.17A
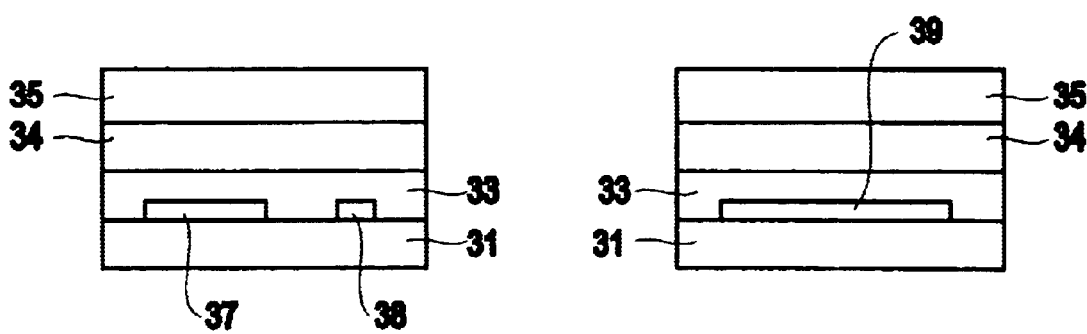
B-B' CROSS SECTION VIEW
FIG.17B
A-A' CROSS SECTION VIEW
FIG.17C

APPARATUS FOR MEASURING A COMPONENT IN A LIQUID SAMPLE

FIELD OF THE INVENTION

The present invention relates to a measurement apparatus and a measurement method for measuring a specified component in a liquid sample using a biosensor utilizing an enzymatic reaction.

BACKGROUND OF THE INVENTION

As a measurement method of a variety of components contained in a biosample and the like, measurement methods employing enzymatic reactions and electrochemical reactions in combination have widely been employed. For example, widely used is a biosensor, which converts a chemical substance in a solution into another substance by the catalytic function of an enzyme and measuring the obtained substance by a redox reaction.

As a method for utilizing such a biosensor, it is general to carry out calibration using a calibration liquid immediately before the use and then carrying out measurement. Carrying out calibration makes it possible to obtain stable measurement values independently of unevenness of the quality of biosensors, alteration of the measurement environments, and fluctuation of the capabilities of sensors with the lapse of time, the like In this case, since the sensitivity of a biosensor has temperature-dependency, measurement error is possibly caused if there is temperature difference between a measurement sample and the calibration liquid. Therefore, a conventional measurement apparatus is so constituted as to comprise a temperature detection means for a measurement sample, a temperature detection means for a calibration liquid, and a temperature correction means and subsequently aim at improving the measurement precision. For example, a urine inspection apparatus equipped with a glucose sensor and an oxygen sensor is disclosed in the Japanese Patent Laid-Open No. 63-1971 and the specification discloses that the temperature correction is carried out for obtaining a correction value at the use time of the apparatus. Further, in the Japanese Patent Laid-Open No. 62-11160 discloses a measurement apparatus employing a fixed enzyme membrane and the specification disclosed that the temperature correction is carried out by measuring the cell temperature at the time of calibration using a standardized liquid and measurement of a sample.

However, in conventional apparatuses described in the foregoing patent specifications, the temperature measurement means are installed in the sensor parts so as to employ methods for carrying out temperature compensation by measuring the temperature of a calibration liquid and a sample brought into contact with the sensors. However, these methods have the following problems.

At first, since a temperature detector is integrated with a sensor that becomes an obstacle to the miniaturization of the measurement apparatus including the sensor.

Secondly, since a temperature detector is integrated with a sensor in the peripheral part of the sensor, in the case of replacing the sensor with a new one owing to the life termination, the temperature detector is required to be replaced simultaneously to result in increase of running cost. In a biosensor using an enzyme, the life of the sensor is relatively short to make it necessary to replace the sensor in a prescribed frequency and it is therefore very important to solve such problems from a viewpoint of lowering the cost.

Thirdly, the temperature measurement of a calibration liquid has sometimes imprecisely been carried out to give a significant error of the sensor measurement value. The sensor is not so capable as to detect the temperature of a calibration liquid immediately after a sensor is brought into contact with the calibration liquid. The detection temperature is fluctuated in a manner that the detection temperature gradually comes closer to the calibration liquid temperature along a curved line determined based on the factors such as the thermal capacity of the sensor itself, the temperature at the point where the sensor is installed, the ambient temperature, the thermal conductivities of the sensor and the materials of the peripheral parts. Consequently, in the case where the contact of the sensor with the calibration liquid is finished before the sensor reaches the calibration liquid temperature, owing to the delay of the detection temperature and the value different from the true temperature is recognized as the calibration liquid temperature and based on the detected value, the temperature correction is carried out to result in measurement error in the value measured by the sensor. Incidentally, regarding such detection delay, description is given in Japanese Patent Laid-Open No. 2-54027 and Japanese Patent Laid-Open No. 2-54028. In these patent specifications, urine measurement apparatuses with the constitution where a sensor is attached to a toilet stool are disclosed and the specifications refer to the problems owing to the delay of the sensor in the detection of urine temperature when the sensor is splashed with urine. The measurement error caused by such delay of the detection of the calibration liquid temperature becomes a significant problem in the case where a biosensor utilizing the enzymatic reactions is employed. That is because the activity of the enzymatic reactions is remarkably changed depending on the temperature.

SUMMARY OF THE INVENTION

The present invention has been developed while taking the above described situation into consideration and aims of saving the installation space by miniaturization of the apparatus and improving the measurement precision while suppressing the running cost in a measurement apparatus employing a biosensor.

The present invention provides a measurement apparatus comprising a biosensor for carrying out measurement of a specified component in a liquid sample using an enzymatic reaction, a computation processing part for obtaining the computed value by computing an output signal of the biosensor, and a container for storing a calibration liquid for calibrating the biosensor, wherein the container is equipped with temperature control means for keeping the calibration liquid at a constant temperature.

Also, the present invention provides a measurement apparatus comprising a biosensor for carrying out measurement of a specified component in a liquid sample using an enzymatic reaction, a computation processing part for obtaining the computed value by computing an output signal of the biosensor, and a container for storing a calibration liquid for calibrating the biosensor, wherein the container is equipped with temperature measurement means for measuring the temperature of the calibration liquid and the computation processing part has a function of correcting the computed value depending on the temperature of the calibration liquid measured by the temperature measurement means.

As described in the paragraph of prior arts, in the case of measurement of the temperature of a calibration liquid in the periphery of a sensor, the detection of the calibration liquid temperature is delayed and a measurement error is sometimes caused. That is attributed to that the limitation of the duration during which the temperature detection means for the calibration liquid is brought into contact with the calibration liquid. To such a problem, the measurement apparatus of the present invention employs the following means for measuring the temperature of the calibration liquid in place of the measurement of the temperature in the sensor periphery: (1) installing temperature control means for keeping a calibration liquid at a constant temperature in a container for storing the calibration liquid or (2) installing a temperature measurement means in a container for storing a calibration liquid and measuring the temperature of the calibration liquid by the means and consequently, the problems derived from the error of the measurement of the calibration liquid temperature in the sensor periphery are solved to heighten the precision of the calibration. In the case where a trace amount of a component in a sample is highly precisely measured, for example, in the case of measurement of urine sugar in a concentration as low as 1 to 5 mg/dl as described somewhere later, the measurement error attributed to the above described detection delay of the calibration liquid temperature becomes impossible to be ignored. According to the present invention, such problems can be solved and highly precise calibration can be performed.

Further, the measurement apparatus provided with a temperature control means has advantages that the circuit for temperature correction can be omitted and that the apparatus can further be miniaturized. For example, if the temperature of a sample, a measurement object, is kept as same as the temperature of the calibration liquid kept at a constant temperature, the temperature correction is made unnecessary. Also, if urine is a measurement sample, since the urine temperature immediately after urination from a human body is about 32° C., no temperature correction is required in the case where measurement is carried out by installing a sensor in a toilet stool and directly dropping urine to the sensor part or in the case where sampled urine is immediately measured, and therefore the present invention can preferably be employed.

Further, the measurement apparatus of the present invention is not required to install any temperature detection means for a sample and a calibration liquid in the sensor part, the apparatus can be miniaturized. For that, the apparatus can be in a handy size or a portable type measurement apparatus or can be suitable as an apparatus to be installed in a narrow space such as a toilet.

Further, the measurement apparatus of the present invention is not required to install any temperature detection means for a sample and a calibration liquid in the sensor part, the temperature measurement means is not required to be replaced simultaneously with the replacement of a sensor and the running cost can thus be lowered as compared with that of conventional measurement apparatuses. In order to effectively utilize such an advantage, the biosensor of the present invention is preferable to be constructed of an enzyme electrode 5 in a detachable manner.

Further, the present invention provides a measurement method for carrying out measurement of a specified component in a liquid sample employing a biosensor utilizing an enzymatic reaction, wherein the measurement method comprises a step of keeping the temperature of a calibration liquid constant, a step of carrying out calibration by bringing the calibration liquid into contact with the biosensor, and a step of obtaining the concentration measured value of a specified component in a liquid sample by carrying out measurement for the liquid sample at the same temperature as that of the calibration liquid.

According to the method, the temperature correction of the calibration value is made unnecessary and the measurement procedure can be simplified. Consequently, even in the case of use by a general user, the measured value is prevented from becoming incorrect by the operation error in the temperature correction for the calibration liquid. Further, there takes place no delay of detection of the calibration liquid temperature, which has been a problem in a conventional technique for measuring the temperature of the calibration liquid in the sensor periphery, and highly precise calibration can be carried out. Further, since no temperature measurement means is required to be installed in the sensor, the apparatus can be miniaturized and the running cost can be lowered.

Further, the present invention provides a measurement method for carrying out measurement of a specified component in a liquid sample employing a biosensor utilizing an enzymatic reaction, wherein the measurement method comprises a step of measuring the temperature of a calibration liquid constant, a step of obtaining a calibration value corrected depending on the temperature of the calibration liquid after carrying out the calibration by bringing the calibration liquid into contact with the biosensor, and a step of obtaining the concentration measured value of a specified component in a liquid sample by carrying out correction using the calibration value after measuring the concentration value of the specified component in the liquid sample.

According to the method, there takes place no delay of detection of the calibration liquid temperature, which has been a problem in a conventional technique for measuring the temperature of the calibration liquid in the sensor periphery, and highly precise calibration can be carried out. Further, since no temperature measurement means is required to be installed in the sensor, the apparatus can be miniaturized and the running cost can be lowered.

The present invention employs means for measuring the temperature of a calibration liquid by installing a temperature control means for keeping the calibration liquid at a constant temperature in the container storing the calibration liquid or installing a temperature measurement means in a container storing the calibration liquid. Hence, detection delay of the liquid temperature, which has been a problem in a conventional technique, is solved and the calibration precision is increased. Further, since no temperature detection means for a sample or the calibration liquid was required to be installed in the sensor part, the apparatus can be miniaturized and made to be a handy size and a portable measurement apparatus or to be installed in a narrow space such as a toilet. Further, it is not necessary to replace the temperature detector simultaneously at the time when the sensor is replaced and consequently the running cost can be lowered as compared with that of a conventional measurement apparatus.

BRIEF DESCRIPTION OF THE DRAWINGS

FIG. 1 is a schematic view of a measurement apparatus of the present invention.

FIG. 2 is a schematic view of a calibration liquid container according to the present invention.

FIG. 3 is a schematic view of a measurement instrument according to the present invention.

FIG. 4 is a diagram showing a circuit constitution of a measurement apparatus according to the present invention.

FIG. 5 is a schematic view of a measurement apparatus according to the present invention.

FIG. 11 is a schematic view of a measurement apparatus according to the present invention.

FIG. 12 is a schematic view of a calibration liquid container according to the present invention.

FIG. 17 is a diagram showing the structure of an enzyme electrode.

DESCRIPTION OF THE PREFERRED EMBODIMENT

Figure 6:
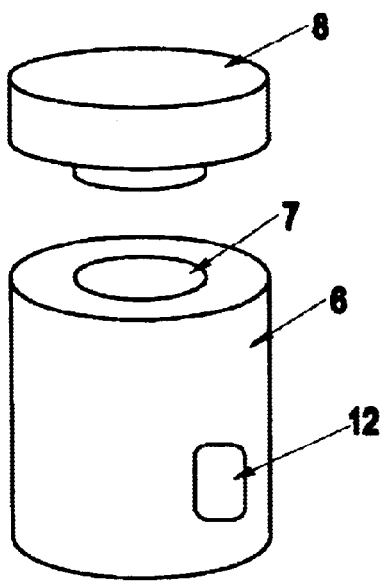
FIG. 6 is a schematic view of a calibration liquid container according to the present invention.

In the present invention, a biosensor is employed for carrying out measurement of a specified component of a liquid sample using the enzymatic reaction. Those of a variety of measurement ways can be employed as the biosensor and usable are those utilizing electrochemical measurement method, absorbance measurement method. Among them, a biosensor utilizing the electrochemical measurement method can provide more outstanding effect on the highly precise calibration performance in the present invention.

As a practical biosensor constitution based on the electrochemical measurement, examples are those respectively comprising an enzyme electrode 5 of a metal film bearing an enzyme layer as a working electrode and a counter electrode installed at a distance from the working electrode to measure the electric current value flowing in the working electrode. The biosensor with such a constitution can employ a method for measurement by converting a specified component in a liquid sample into another substance by the enzymatic reaction and measuring the generated amount of the converted substance. For example, in the case of a glucose biosensor, glucose is oxidized by a glucose oxidase (GOX) to generate gluconic acid and hydrogen peroxide and the generated hydrogen peroxide is measured to quantitatively measure the glucose concentration. Further, other than the method, a method applicable involves steps of measuring the decrease value of oxygen reduction current following to the decrease of oxygen in the periphery of the enzyme layer and quantitatively measuring the concentration of the glucose concentration.

One example of a biosensor composing a measurement apparatus of the present invention is illustrated in FIG. 17. A working electrode 37, a counter electrode 38, and a reference electrode 39 are formed on an insulating substrate 31. A bonding layer 33, a fixed enzyme layer 34, and a limited permeation layer 35 are formed in this order on the working electrode 37, the counter electrode 38, and the reference electrode 39.

As a material for the insulating substrate 31, usable are those of mainly materials with high insulation property such as ceramics, glass, quartz, plastics and the like. The materials are preferable to be excellent in water-proofness, heat resistance, chemical resistance, and adhesion strength to electrodes. As materials for the working electrode 37 and the counter electrode 38, for example, those mainly containing platinum, gold, silver, carbon and the like are usable. Among them, preferable to be used is platinum which is excellent in the chemical resistance and hydrogen peroxide detection characteristics. On the other hand, for the reference electrode 39 silver/silver chloride electrode is preferable to be used. The bonding layer 33 is formed in order to improve the adhesion strength (bonding force) of the fixed enzyme layer 34 thereon and the insulating substrate 31 to the respective electrodes and produced from mainly a silane-coupling agent. For example, the layer can be formed by spin coating with a silane coupling agent solution.

The fixed enzyme layer 34 is composed of an organic polymer as a mother material and an enzyme having a catalytic function and fixed thereon. The fixed enzyme layer 34 is formed by, for example, dropwise titrating a solution containing a variety of enzyme, a protein cross-linking agent such as glutaraldehyde and the like, and albumin on the bonding layer 33 and then carrying out spin-coating. Albumin protects a variety of the enzymes from the reaction by the cross-linking agent and becomes a substrate of protein as well. As the enzymes, usable are those which produce hydrogen peroxide as a product by the catalytic reaction or consume oxygen, such as lactic acid oxidase, glucose oxidase, uric acid oxidase, galactose oxidase, lactose oxidase, sucrose oxidase, ethanol oxidase, methanol oxidase, starch oxidase, amino acid oxidase, monoamine oxidase, cholesterol oxidase, choline oxidase, pyruvic acid oxidase, and the like.

In this case, two or more kinds of enzymes may simultaneously be employed. Creatininase, creatinase, and sarcosine oxidase are examples. Using these enzymes makes detection of creatinine possible. Further, an enzyme and a coenzyme may be used together. Examples are 3-hydroxybutyric acid dehydrogenase and nicotinamidoadeninedinucleotide (NAD). Using these enzymes make detection of 3-hydroxybutyric acids possible. Further, an enzyme and an electron mediator may be used together. In this case, the electron mediator reduced by the enzyme is oxidized on the electrode surface and the oxidation current value generated at that time is measured. Examples are glucose oxidase and potassium ferricyanide. Glucose detection is made possible by using them.

As described above, the fixed enzyme layer 34 is not particularly restricted as long as the layer contains at least enzymes and has a function of converting an object substance to be measured to hydrogen peroxide or the like, an electrode-susceptive substance.

Incidentally, the formation method of the fixed enzyme layer 34 is not particularly restricted as long as the method is capable of forming a film with a uniform film thickness, and other than the spin-coating method, a screen-printing method is applicable.

The limited permeation layer 35 is to limit the excess diffusion of a chemical substance, which is an object of the measurement, to increase the possible measurement range to a high concentration and to improve the precision of the measurement in the low concentration region. Further the limited permeation layer 35 works as to limit the permeation of pollutant substances and interfering substances reactive to the electrode. Protein is among the pollutant substances and ascorbic acid, ureic acid, p-acetaminophen, and the like. The limited permeation layer 35 is preferably made of fluoroalcohol ester with methacrylic acid resin. The fluoroalcohol ester with methacrylic acid resin means methacrylic acid resin partially or entirely esterified with fluoroalcohol and the fluoroalcohol is alcohol of which hydrogen atoms are entirely or at least one hydrogen-atom is substituted with fluorine. Usable examples are poly (1H, 1H-perfluorooctyl methacrylate), poly (1H, 1H, 2H, 2H-perfluorodecyl methacrylate) and the like. Poly (1H, 1H-perfluorooctyl methacrylate) is defined as a polymer of methacrylic acid partially or entirely esterified with 1H, 1H-perfluorooctyl alcohol.

The limited permeation layer 35 can be formed by dropwise titrating a solution containing perfluorocarbon such as a perfluorohexane and the like as a solvent and a fluoroalcohol ester with methacrylic acid resin diluted with the solvent on the fixed enzyme layer 34 in which the enzyme having a catalytic function is fixed and then carrying out a spin coating method or the like.

In the case where the enzyme electrode 5 is used as a glucose sensor, the limited permeation layer 35, which is the outermost layer, limits the diffusion speed of glucose. The diffused glucose is catalytically reacted in the fixed enzyme layer 34 employing the glucose oxidase to generate hydrogen peroxide and gluconolactone. The glucose concentration can be known by measuring the oxidation current when hydrogen peroxide between them reaches the working electrode 37.

As described above, in the case of employing an enzyme electrode equipped with the limited permeation layer with a specified structure, the measurement sensitivity is remarkably improved as compared with that of a conventional sensor. For example, in the case where the foregoing biosensor is used as a urine sugar sensor for measurement of glucose in urine (urine sugar), in terms of the measurement lower limit of the urine sugar, a conventional technique has had a limitation of 50 mg/dl, whereas the sensor of the present invention can detect even to 1 to 5 mg/dl. However, when the measurement is carried out such a low concentration region, the effect of the calibration liquid temperature on the urine sugar measurement value is relatively increased and regarding the calibration, the precision at a high level is to be required. At that point, according to the present invention, precise calibration sufficiently high enough to meet the foregoing requirement can be achieved, so that the sensor of the present invention can preferably usable for such purposes. As described above, the present invention is especially remarkably effective if the enzyme electrode equipped with the limited permeation layer of the foregoing specified structure is employed and makes it possible to measure urine sugar of human being whose urine sugar value is within a normal range or who is in preliminary stage of diabetics, which has been impossible by a conventional sensor, by employing the enzyme electrode for a urine sugar sensor and makes it possible to collect the data useful for prevention of diabetics.

The present invention is much more effective if it is applied to a sensor aiming to measure a body fluid of a living body, especially, urine. The temperature of urine is approximately constant, around 32° C., immediately after urination. For that, according to the present invention wherein the temperature of the calibration liquid is previously to be known, accurate calibration is actualized with a simple constitution.

The calibration liquid of a biosensor of the present invention means a liquid for carrying out calibration by being brought into contact with an electrode part of a sensor before use. An object substance to be measured in a known concentration is dissolved in the calibration liquid. Since the sensor output of the biosensor is obtained as voltage or current, the calibration liquid is preferable to contain an electrolytic substance with a high dissociation constant and a substance having pH buffering function (hereinafter referred as to a buffer substance). As the electrolytic substance, generally used are sodium chloride, potassium chloride, sodium sulfate, and potassium sulfate, however any substance may be used as long as it has a high dissociation constant and is non-reactive or hardly reactive on the working electrode, an electrode. As the buffer substance, generally used are, for example, N-tris (hydroxymethyl)-methyl-2-aminoethenesulfonic acid (hereinafter abbreviated as TES) and N-2-(hydroxymethyl) piperazine-N'-2-ethanesulfonic acid, however as same as the electrolytic substance, any substance may be used as long as it is non-reactive or hardly reactive on the working electrode. The calibration method may be a two-point calibration method by carrying out calibration at the measurement value at a prescribed concentration and at the zero point or three-point calibration method by the measurement values at 2 or more points.

The calibration liquid container of the present invention is provided with temperature control means for keeping the temperature of the calibration liquid constant or temperature measurement means for measuring the temperature of the calibration liquid. The temperature control means can be constituted by combining temperature increasing means such as a heater and control means by PID or the like and, if necessary, temperature decreasing means such a cooling pipe can be employed. A temperature sensor, for example, thermocouple type one, may be employed for the temperature measurement means. The temperature measurement means is installed as to be brought into contact with the calibration liquid stored in a container or as to touch the wall face of container whose temperature is stably same as that of the calibration liquid.

Hereinafter, preferable embodiments of the present invention will be described with the reference to figures.

(First embodiment)

This embodiment will be described with the reference to figures. As shown in FIG. 1, a measurement apparatus according to the embodiment is composed of a biosensor, a computation processing part, a measurement apparatus (FIG. 1(a)) including a data informing part 2, and a calibration liquid container (FIG. 1(b)).

Figure 22:
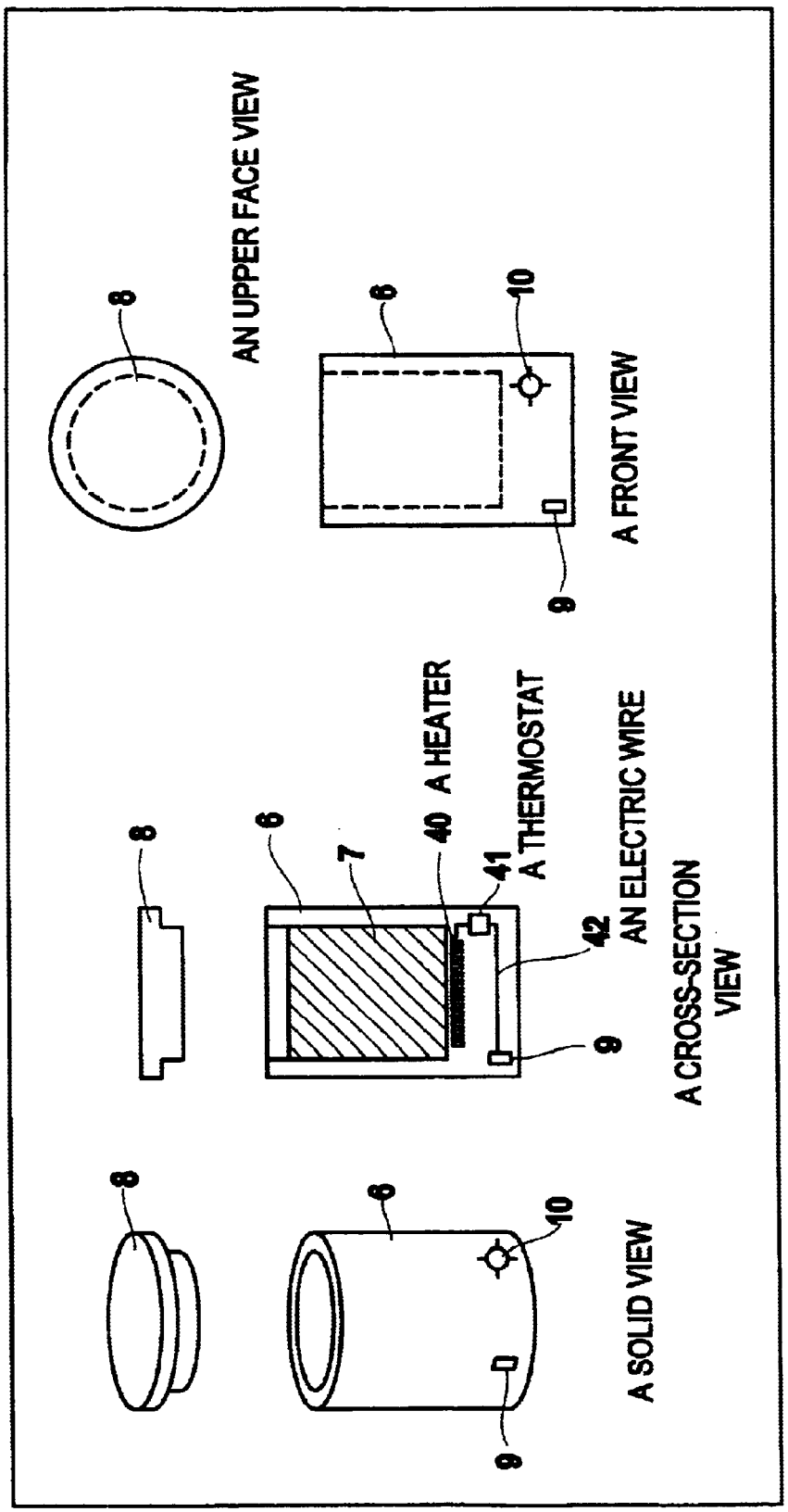
FIG. 22 is a schematic view of a calibration liquid container according to the present invention.

As shown in FIG. 2, the calibration liquid container is composed of a container 6 and a cover 8 and an electric power switch 9 and a temperature adjustment switch 10 are installed in the container 6. The container 6 is filled with a calibration liquid 7. The more detailed structure of the calibration liquid container shown in FIG. 2 is as illustrated in FIG. 22. The temperature control part of the calibration liquid container is composed of a heater 40, a thermostat 41, an electric wire 42, the electric power switch 9, and the temperature adjustment switch 10 and by adjusting the temperature adjustment switch 10, the temperature of the calibration liquid container is adjusted. Any temperature decreasing means is not specifically installed in the container, temperature-decreasing means may be installed by laying a cooling pipe around the circumference of the container.

On the other hand, the measurement apparatus has a structure as shown in FIG. 3 and is equipped with an enzyme electrode 5 in the tip part and a circuit (not illustrated) for carrying out computation processing the output from the enzyme electrode 5. An electric power switch 3, a calibration switch 4, a data informing part 2, and a calibration liquid temperature setting switch 11 are respectively installed in a main body 1.

The circuit constitution of the measurement apparatus is shown in FIG. 4. The enzyme electrode 5 is connected with an electrochemical measurement circuit part 21. Although a potentiostat is employed for the electrochemical measurement circuit part 21 in the present embodiment, the circuit is not particularly restricted as long as it is capable of applying the constant potential to the enzyme electrode 5 and measuring the current value. The output signal transmitted via the electrochemical measurement circuit part 21 is inputted to the data processing part 22. The data processing part 22 has a function of computing values of the measurement based on the output signal from the enzyme electrode 5. For example, the data processing part 22 operates as to convert the foregoing electric signal to an analog signal or a digital signal and computes the measurement value. The constitution of the data processing part 22 is not particularly restricted as long as it has a computation part such as a microprocessor capable of processing the signals from the electrochemical measurement circuit part 21.

The signal processed through the data processing part 22 is informed as a measurement value by the data informing part 2. The data informing part 2 is not particularly restricted as long as it has a function of informing the data processed by the data processing part 22. As the informing means, the present embodiment employs display on a display window installed in the main body, however, other than that, applicable are any styles capable of informing the results by sound, light, vibration, color, light and the like.

The respective parts having the above-described functions are electrically connected with wiring 24.

Figure 9:
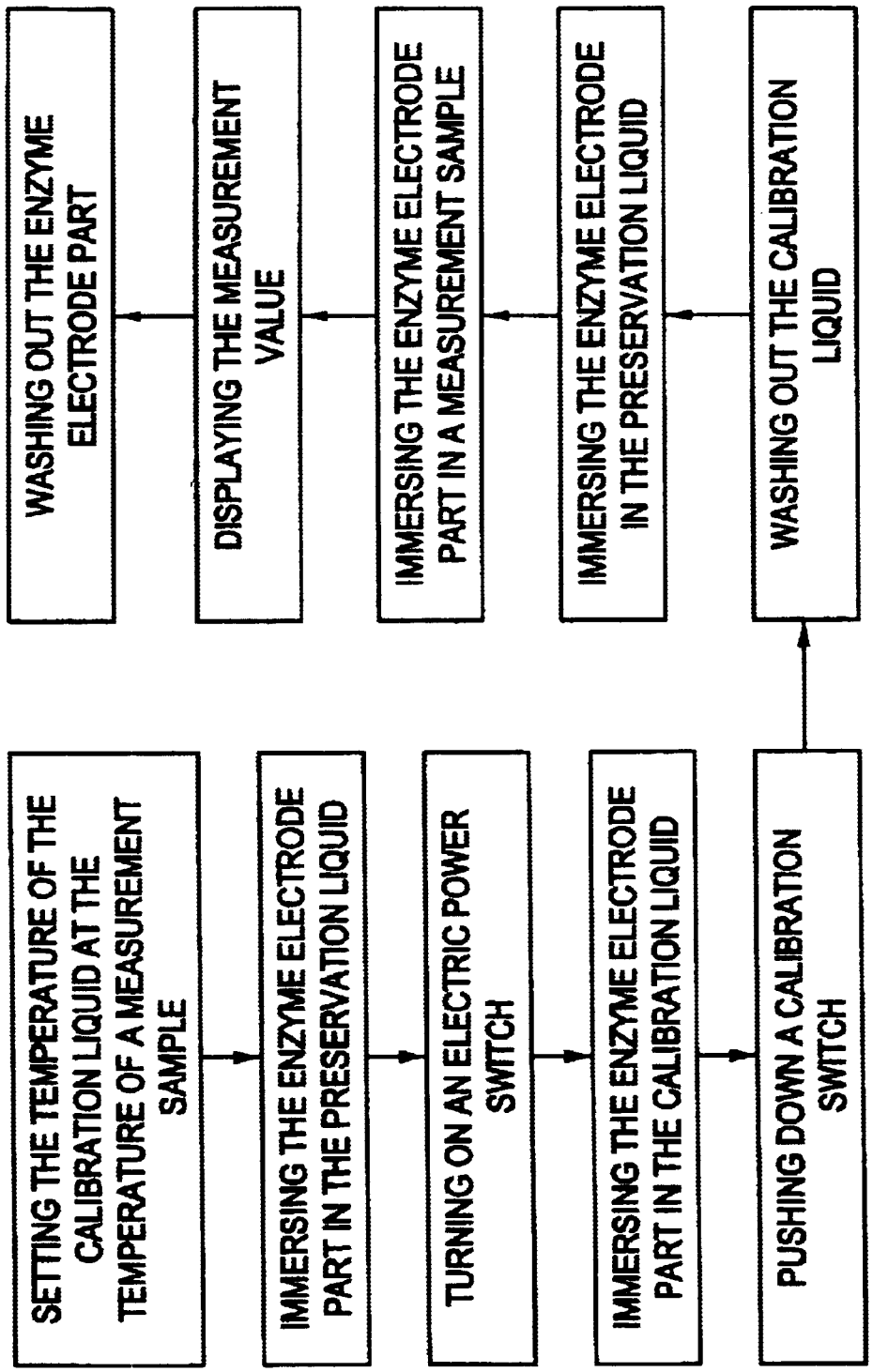
FIG. 9 is a diagram showing the measurement procedure using a measurement apparatus according to the present invention.

The measurement method using the measurement apparatus of the present embodiment will be described with the reference to FIG. 9. At first, the electric power switch 9 of the calibration liquid container is turned on and the temperature of the temperature adjustment switch 10 is set as the same value as that of the measurement sample. Next, the enzyme electrode 5 of measurement apparatus is immersed in a preservation liquid (not illustrated) and then the electric power switch 3 of the measurement apparatus is turned on. After the calibration liquid is confirmed to be at the set temperature, the enzyme electrode 5 is immersed in the calibration liquid 7 filling the calibration liquid container shown in FIG. 2 and the calibration switch 4 of the measurement apparatus is pushed down to carry out calibration of the calibration liquid measurement apparatus. The calibration method may be by 2-point calibration of the measurement value at the prescribed concentration and at the zero point or by 3-point calibration of the measurement values at 2 or more points. After the calibration liquid on the surface of the enzyme electrode 5 is washed out, the enzyme electrode 5 is immersed in the preservation liquid. Next, the enzyme electrode 5 is immersed in a measurement sample to carry out measurement. On completion of the measurement, the enzyme electrode part 5 is washed and turned back to the preservation liquid and then next measurement is to be carried out. The measurement method as described above can provide a highly precise measurement value.

(Second embodiment)

Figure 23:
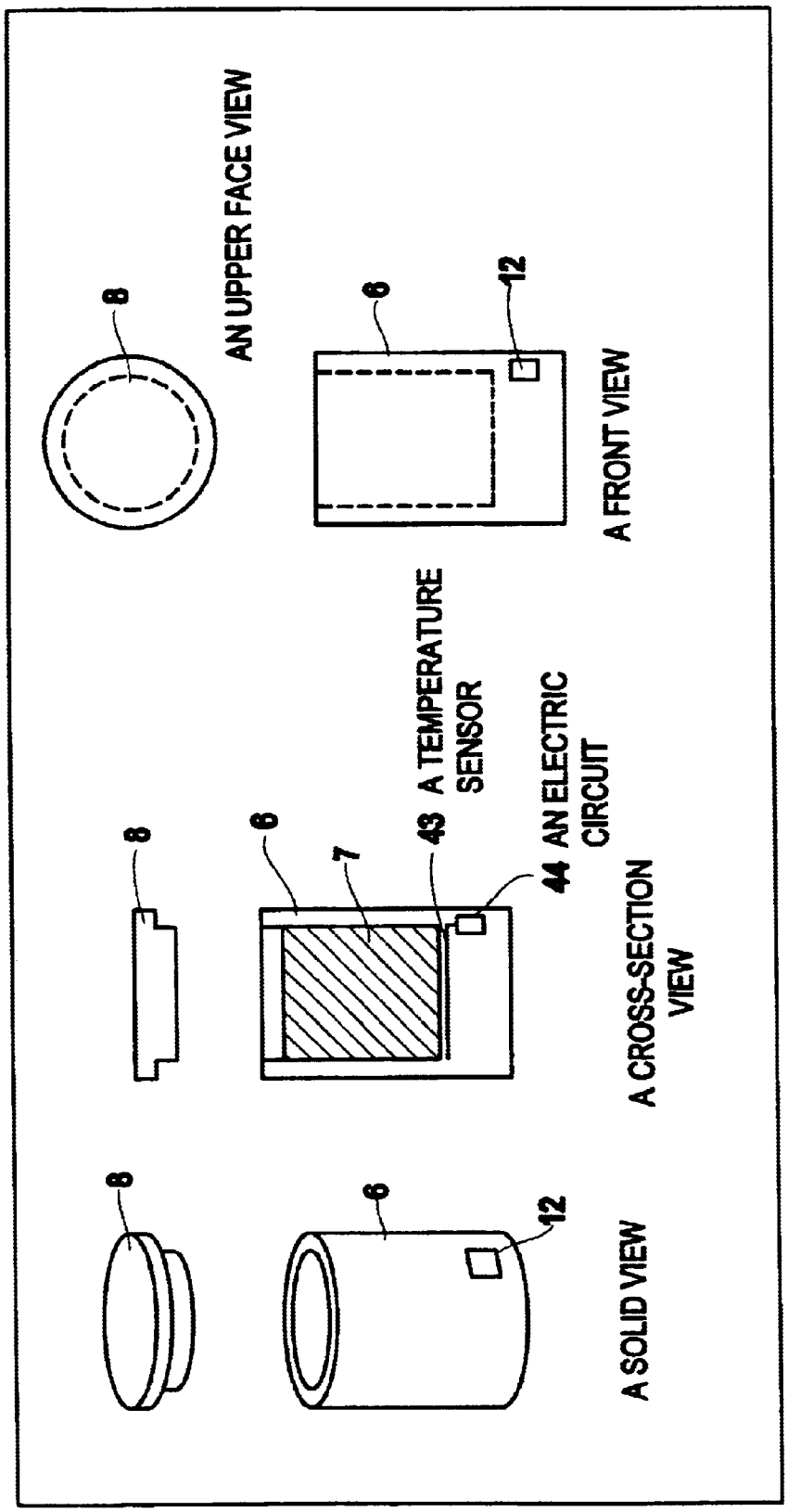
FIG. 23 is a schematic view of a calibration liquid container according to the present invention.

This embodiment will be described with the reference to figures. As shown in FIG. 5, a measurement apparatus according to the embodiment is composed of a biosensor, a computation processing part, a measurement apparatus (FIG. 1(a)) including a data informing part, and a calibration liquid container (FIG. 1(b)). As shown in FIG. 6, the calibration liquid container is composed of a container 6 and a cover 8 and a thermometer 12 is installed in the container 6. The container 6 is filled with a calibration liquid 7. The more detailed structure of the calibration liquid container is as illustrated in FIG. 23 and the thermometer 12 in the calibration liquid container is composed of a thermocouple type temperature sensor 43 and an electric circuit 44.

Figure 7:
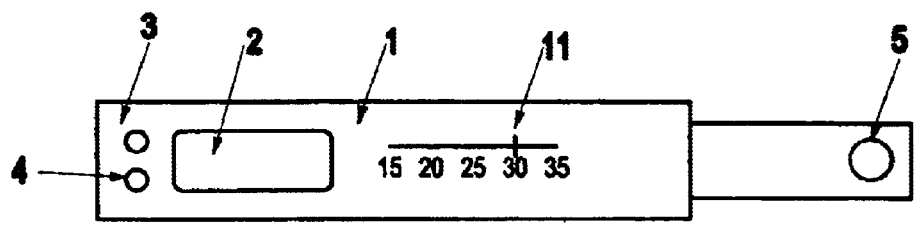
FIG. 7 is a schematic view of a measurement instrument according to the present invention.

On the other hand, the measurement apparatus has a structure as shown in FIG. 7 and is equipped with an enzyme electrode 5 in the tip part and a circuit (not illustrated) for carrying out computation processing the output from the enzyme electrode 5. An electric power switch 3, a calibration switch 4, a data informing part 2, and further a calibration liquid temperature setting switch 11 for inputting the temperature of the calibration liquid are respectively installed in a main body 1 in the same manner as the first embodiment.

Figure 8:
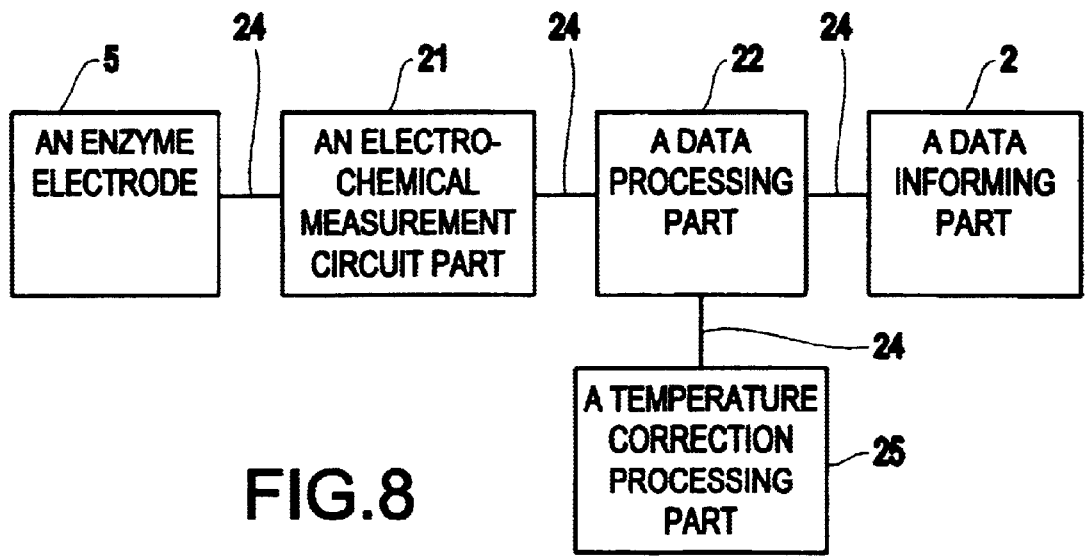
FIG. 8 is a diagram showing of a circuit constitution of a measurement apparatus according to the present invention.

The circuit constitution of the measurement apparatus is shown in FIG. 8. The enzyme electrode 5 is connected with an electrochemical measurement circuit part 21. Although a potentiostat is employed for the electrochemical measurement circuit part 21 in the present embodiment, the circuit is not particularly restricted as long as it is capable of applying the constant potential to the enzyme electrode 5 and measuring the current value. The output signal transmitted via the electrochemical measurement circuit part 21 is inputted to the data processing part 22. The data processing part 22 has a function of computing the measurement value based on the output signal from the enzyme electrode 5, and for example, the data processing part 22 operates as to convert the foregoing electric signal to an analog signal or a digital signal and computes the measurement value. The constitution of the data processing part 22 is not particularly restricted as long as it has a computation part such as a microprocessor capable of processing the signals from the electrochemical measurement circuit part 21. The computation in the data processing part is carried out while taking temperature correction by a temperature correction processing part 25 into consideration. Thus, a highly precise calibration with the temperature of the calibration liquid taken into consideration can be realized.

The signal processed through the data processing part 22 is informed as a measurement value by the data informing part 2. The data informing part 2 is not particularly restricted as long as it has a function of informing the data processed by the data processing part 22. As the informing means, the present embodiment employs display on a display window installed in the main body, however, other than that, applicable are any styles capable of informing the results by sound, light, vibration, color, light and the like.

The respective parts having the above-described functions are electrically connected with wiring 24.

Figure 10:
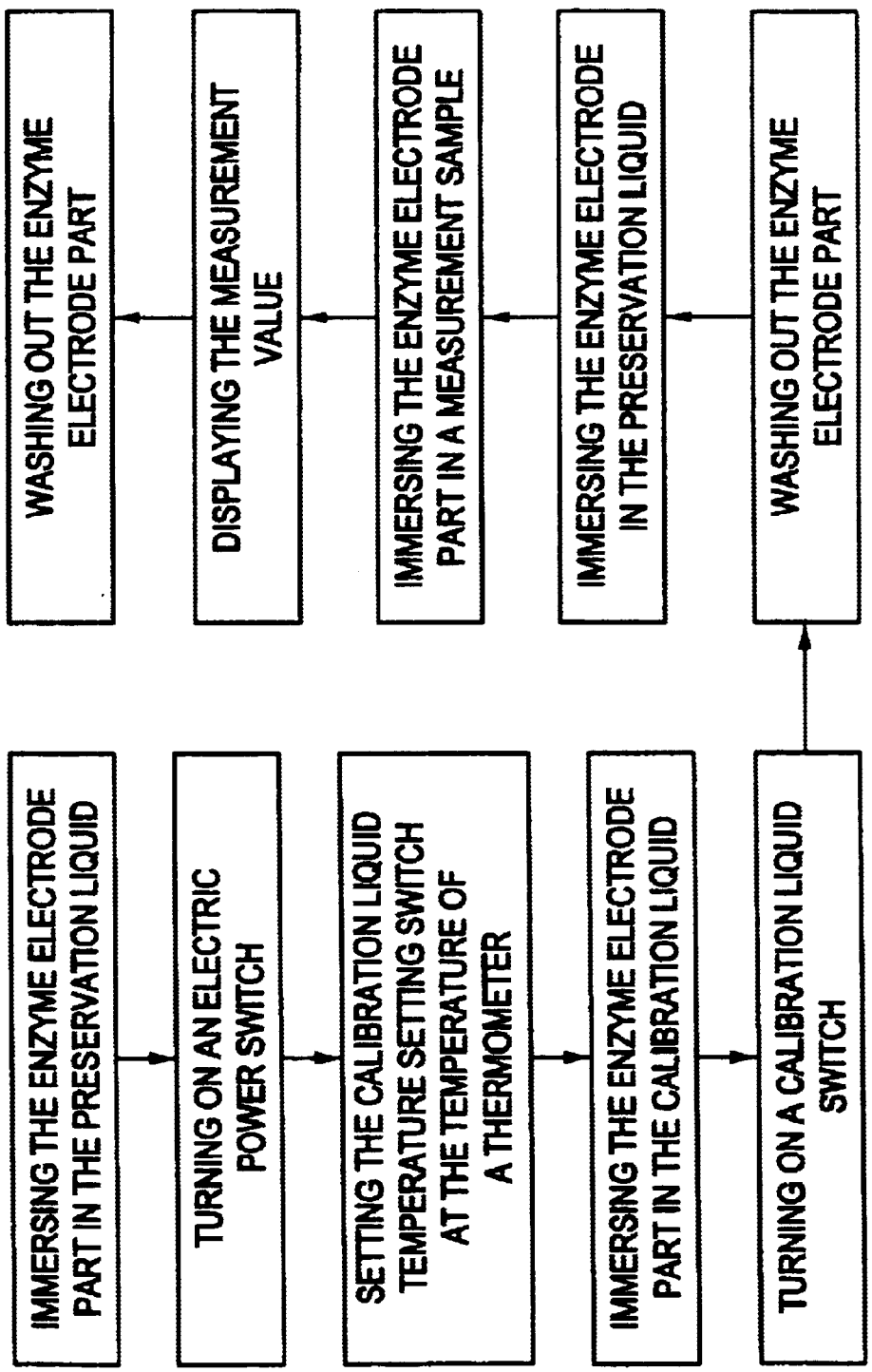
FIG. 10 is a diagram showing the measurement procedure using a measurement apparatus according to the present invention.

The measurement method using the measurement apparatus of the present embodiment will be described with the reference to FIG. 10. At first, the enzyme electrode 5 part of the measurement apparatus is immersed in a preservation liquid and the electric power switch 3 is turned on. Successively, the calibration liquid temperature setting switch 11 is set as the same the temperature value as that the thermometer 12 installed in the calibration liquid container displays. Next, the enzyme electrode is immersed in the calibration liquid and the calibration switch is pushed down to carry out calibration of the liquid component measurement apparatus. After the calibration liquid on the surface of the enzyme electrode 5 is washed out, the enzyme electrode 5 is immersed in the preservation liquid. Next, the enzyme electrode 5 is immersed in a measurement sample to carry out measurement. On completion of the measurement, the enzyme electrode part is washed and turned back to the preservation liquid and then next measurement is to be carried out. The measurement method as described above can provide a highly precise measurement value.

(Third embodiment)

Figure 13:
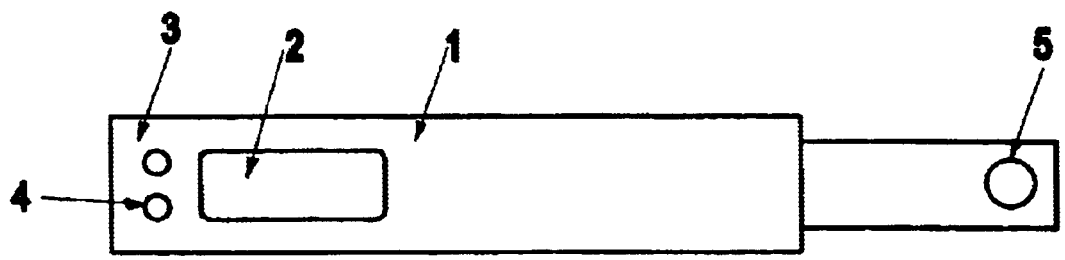
FIG. 13 is a schematic view of a measurement instrument according to the present invention.
Figure 14:
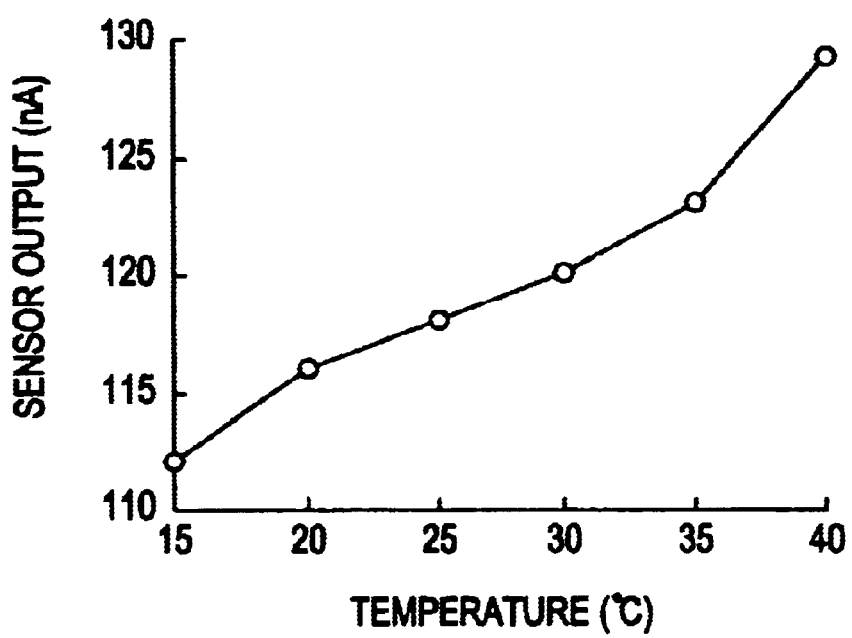
FIG. 14 is a graph showing the temperature dependency of the sensor output.

Although the measurement apparatus and the calibration liquid container are mutually made independent in the second embodiment, they may be electrically connected with an electric wire 24. FIGS. 11 to 13 are schematic figures of a measurement apparatus with such a constitution. In FIG. 11, a measurement apparatus and a calibration liquid container are mutually electrically connected with an electric wire 24. As shown in FIG. 12, the calibration liquid container is composed of a container 6 and a cover 8 and a thermocouple type thermometer 12 is installed in the container 6. The container 6 is filled with a calibration liquid 7. The measurement apparatus has a structure as illustrated in FIG. 13 and is provided with an enzyme electrode 5 at the tip end part and comprises a circuit (not illustrated) for carrying out computation processing the output from the enzyme electrode 5. An electric power switch 3, a calibration switch 4, and a data informing part 2 are respectively installed in a main body 1. Differing from the second embodiment, the present embodiment employs no calibration liquid temperature setting switch 11 for inputting the temperature of the calibration liquid and the data of the calibration liquid temperature is to be directly transmitted to the measurement apparatus through the electric wire 24 connected to the calibration liquid container.

The measurement method employing the measurement apparatus is approximately the same as that of the second embodiment and a different point is that the setting of the calibration liquid temperature-setting switch 11 is made no need. Although, the apparatus of the present embodiment slightly sacrifices the handy property of the measurement apparatus, it is provided with improved operational property since the operation of setting the calibration liquid temperature is made no need.

EXAMPLES

Hereinafter, the present invention will be described more particularly according to examples. Incidentally, the calibration liquids used in the following examples and the comparative examples were all a solution of 200 mg/dl glucose. That is, the solution used contained 200 mg/dl glucose dissolved in a buffer solution of 1 mM TES [N-tris (hydroxymethyl)-methyl-2-aminoethanesulfonic acid] at pH 7 containing 150 mM sodium chloride.

Example 1

In the present example, a measurement apparatus with the same constitution as shown in FIGS. 1 to 3 was manufactured and evaluation was performed. At first, a working electrode (surface area of 7 mm$^2$) made of platinum, a counter electrode (surface area of 4 mm$^2$), and two reference electrodes (surface area of 1 mm$^2$) of silver/silver chloride were formed on a quartz substrate of 10 mm×6 mm size. Continuously, after a bonding layer was formed by spin coating using a 1 v/v% γ-aminopropyltriethoxysilane solution, a fixed enzyme layer was formed by spin coating using a 22.5 w/v% albumin solution containing glucose oxidase and 1 v/v% glutaraldehyde to produce an electric current detection type enzyme electrode.

Continuously, using the enzyme electrode, a liquid component measurement apparatus was manufactured. The liquid component measurement apparatus was manufactured by mounting an electrochemical measurement circuit part, a data processing part and a date display part in the inside of a main body, connecting them through wiring, installing an electric power switch and a calibration switch for operation in the front face of a main body, and further mounting the foregoing enzyme electrode in the main body and connecting the enzyme electrode with the electrochemical measurement circuit part with wiring. The enzyme electrode was installed in a manner to be detached from the main body and was made properly replaceable.

On the other hand, a calibration liquid container storing a calibration liquid for carrying out calibration of the enzyme electrode was made to have the structure as shown in FIG. 2.

Next, description will be given regarding the operation procedure of the measurement apparatus comprising the foregoing liquid component measurement apparatus and the calibration liquid container and the results of glucose measurement in urine carried out using the measurement apparatus.

At first, the electric power switch of the calibration liquid container was turned on and the temperature of the temperature adjustment switch was set at the same value, 32° C., as that of a measurement sample. Next, the enzyme electrode part of the liquid component measurement apparatus was immersed in a preservation solution of a TES [N-tris (hydroxymethyl)-methyl-2-aminoethanesulfonic acid] acid solution at pH 7 containing 150 mM sodium chloride and the electric power switch was turned on. After it was confirmed that the calibration liquid was at the set temperature, the enzyme electrode was immersed in the calibration liquid and the calibration switch was pushed down to carry out calibration of the liquid component measurement apparatus. Then, after the calibration liquid on the enzyme electrode surface was washed out, the enzyme electrode was turned back to the foregoing preservation solution and then immersed in a measurement sample to carry out measurement. On completion of the measurement, the enzyme electrode part was washed and turned back to the preservation solution to be made ready for the next measurement.

The temperature dependency of the measurement values of the foregoing measurement apparatus was shown in FIG.

14. In the Figure, the axis of abscissas shows the temperature of the measurement sample and the axis of ordinates shows the sensor output. The measurement sample was a 1000 mg/dl glucose solution. According to the plotted results, the measurement values were found considerably fluctuated depending on the temperature.

Next, using the measurement apparatus, an actual urine sample containing 21 mg/dl glucose at 32° C. was measured. The same sample was measured repeatedly 10 times and the fluctuation among the measurement values was evaluated. Incidentally, in order to prevent temperature decrease of the actual urine sample during the evaluation, the sample was put in a thermostat apparatus to be evaluated.

Comparative Example 1

Using a measurement apparatus comprising a calibration liquid container provided with no temperature adjustment function, glucose measurement was carried out in the same manner as example 1.

Figure 15:
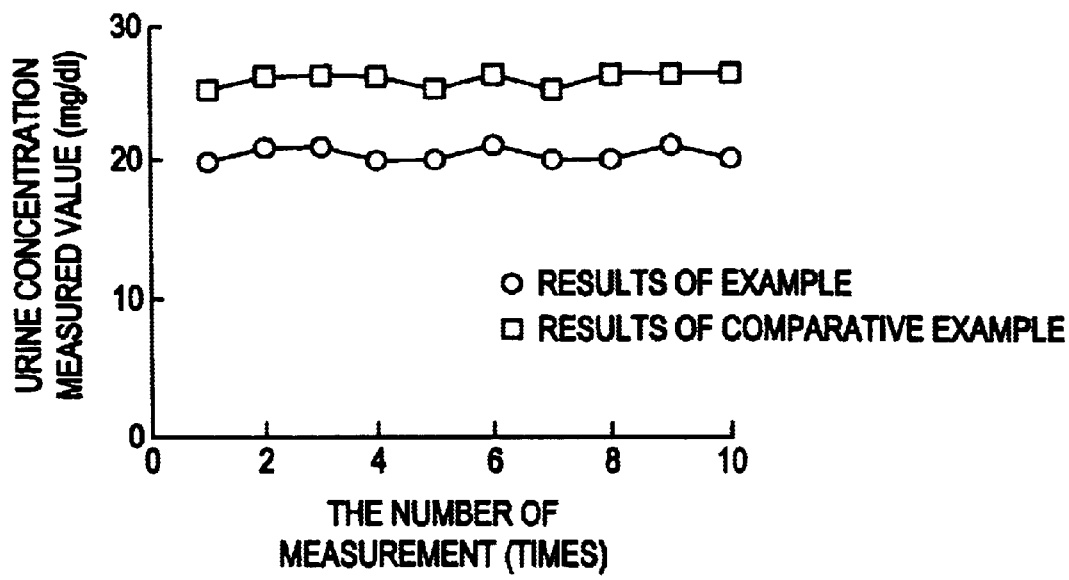
FIG. 15 is a graph showing the urine sugar measurement results using a measurement apparatus according to the present invention.

The measurement results of the example 1 and the comparative example 1 were shown in FIG. 15. In Figure, the circle marks and the square marks show the results of the example 1 and the comparative example 1, respectively. The measurement of the example 1 resulted in 21±0.8 mg/dl measurement values, which were the same value as the actual concentration (21 mg/dl). On the other hand, the measurement values of the comparative example 1 were 26±0.9 mg/dl. It was made clear that the measurement at a high precision can be performed by installing a temperature adjustment function in the calibration liquid container.

Example 2

In the present example, a measurement apparatus with the same constitution as shown in FIGS. 5 to 7 was manufactured and evaluation was performed. At first, a working electrode (surface area of 7 mm$^2$) made of platinum, a counter electrode (surface area of 4 mm$^2$), and two reference electrodes (surface area of 1 mm$^2$) of silver/silver chloride were formed on a quartz substrate of 10 mm×6 mm size. Continuously, after a bonding layer was formed by spin coating using a 1 v/v% γ-aminopropyltriethoxysilane solution, a fixed enzyme layer was formed by spin coating using a 22.5 w/v% albumin solution containing glucose oxidase and 1 v/v% glutaraldehyde to produce an electric current detection type enzyme electrode.

Continuously, using the enzyme electrode, a liquid component measurement apparatus was manufactured. The liquid component measurement apparatus was manufactured by mounting an electrochemical measurement circuit part, a data processing part equipped with a temperature correction processing part and a date display part in the inside of a main body, connecting them through wiring, providing an electric power switch for activating these parts, a calibration switch and a calibration liquid temperature setting switch in the front face of a main body, and further mounting the foregoing enzyme electrode in the main body and connecting the enzyme electrode with the electrochemical measurement circuit part with wiring. The enzyme electrode was installed in a manner to be detached from the main body and was made properly replaceable.

On the other hand, a calibration liquid container storing a calibration liquid for carrying out calibration of the enzyme electrode was made to have the structure as shown in FIG. 6.

Next, description will be given regarding the operation procedure of the measurement apparatus and the results of glucose measurement in urine carried out using the measurement apparatus.

In the following measurement method, it was presumed that the temperature of the object substance to be measured was previously known and the temperature of the object substance to be measured was stored in a memory of the data processing part of the measurement apparatus.

Next, the enzyme electrode part of the liquid component measurement apparatus was immersed in a preservation solution of a TES [N-tris (hydroxymethyl)-methyl-2-aminoethanesulfonic acid] at pH 7 containing 150 mM sodium chloride and the electric power switch was turned on. Continuously, the calibration liquid temperature-setting switch of the liquid component measurement apparatus was set at the temperature, which the thermometer installed in the calibration liquid container indicated. Then, the enzyme electrode was immersed in the calibration liquid and the calibration switch was pushed down to carry out calibration of the liquid component measurement apparatus. Next, after the calibration liquid on the enzyme electrode surface was washed out, the enzyme electrode was turned back to the foregoing preservation solution and then immersed in a measurement sample to carry out measurement. On completion of the measurement, the enzyme electrode part was washed and turned back to the preservation solution to be made ready for the next measurement.

Using the measurement apparatus, an actual urine sample containing 21 mg/dl glucose at 32° C. was measured. The calibration liquid temperature-setting switch was set at 24° C. and the measurement sample temperature-setting switch was set at 32° C. The same sample was measured repeatedly 10 times and the fluctuation among the measurement values was evaluated. Incidentally, in order to prevent temperature decrease of the actual urine sample during the evaluation, the sample was put in a thermostat apparatus to be evaluated.

Comparative Example 2

As reference experiment for the example 2, the following two types of apparatuses were made ready and measurement was performed.

(a) Using a measurement apparatus having no temperature correction processing part, measurement was carried out in the same manner as the example 2.
(b) A measurement apparatus comprising a thermometer installed in the enzyme electrode part but not in the calibration liquid container part side was used. At the time of immersing the enzyme electrode part in the calibration liquid to carry out calibration, the calibration liquid temperature-setting switch of the liquid component measurement apparatus was set at the temperature, which the thermometer indicated. Other than that, the measurement procedure was made same as that of the example 2.

Figure 16:
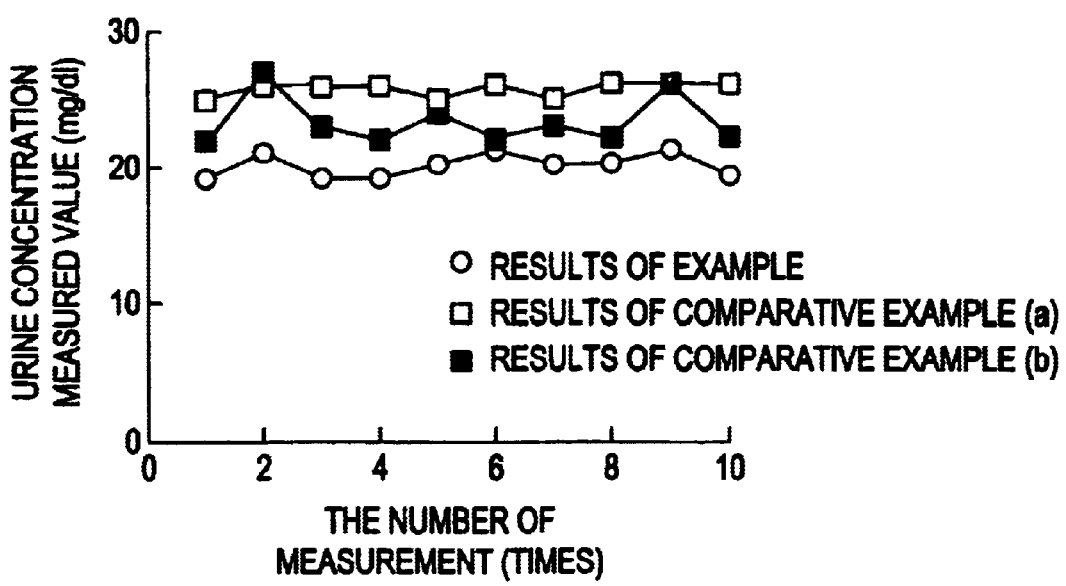
FIG. 16 is a graph showing the urine sugar measurement results using a measurement apparatus according to the present invention.

The measurement results of the example 2 and the comparative example 2 were shown in FIG. 16. The measurement of the example 2 resulted in 21±0.8 mg/dl measurement values, whereas the measurement values of the comparative example 2 were 26±0.9 mg/dl for experiment (a) and 23±1.8 mg/dl for experiment (b). According to the results, it was made clear that the measurement values with a high precision can be obtained by installing a thermometer in the calibration liquid container side.

Example 3

In the present example, a measurement apparatus with the same constitution as shown in FIGS. 1 to 3 was manufactured and evaluation was performed. At first, a working electrode (surface area of 7 mm²) made of platinum, a counter electrode (surface area of 4 mm²), and two reference electrodes (surface area of 1 mm²) of silver/silver chloride were formed on a quartz substrate of 10 mm×6 mm size. Continuously, after a bonding layer was formed by spin coating using a 1 v/v% γ-aminopropyltriethoxysilane solution, a fixed enzyme layer was formed by spin coating using a 22.5 w/v% albumin solution containing glucose oxidase and 1 v/v% glutaraldehyde to produce an electric current detection type enzyme electrode.

Continuously, using the enzyme electrode, a liquid component measurement apparatus was manufactured. The liquid component measurement apparatus was manufactured by mounting an electrochemical measurement circuit part, a data processing part and a date display part in the inside of a main body, connecting them through wiring, installing an electric power switch and a calibration switch for operation in the front face of a main body, and further mounting the foregoing enzyme electrode in the main body and connecting the enzyme electrode with the electrochemical measurement circuit part with wiring. The enzyme electrode was installed in a manner to be detached from the main body and was made properly replaceable.

On the other hand, a calibration liquid container storing a calibration liquid for carrying out calibration of the enzyme electrode was made to have the structure as shown in FIG. 2.

Next, description will be given regarding the operation procedure of the measurement apparatus and the results of glucose measurement in urine carried out using the measurement apparatus.

At first, the electric power switch of the calibration liquid container was turned on and the temperature of the temperature adjustment switch was set at the same value, 32° C., as that of a measurement sample. Next, the enzyme electrode part of the liquid component measurement apparatus was immersed in a preservation solution of a TES [N-tris(hydroxymethyl)-methyl-2-aminoethanesulfonic acid] buffer solution at pH 7 containing 150 mM sodium chloride and the electric power switch was turned on. After it was confirmed that the calibration liquid was at the set temperature, the enzyme electrode was immersed in the calibration liquid and the calibration switch was pushed down to carry out calibration of the liquid component measurement apparatus. Then, after the calibration liquid on the enzyme electrode surface was washed out, the enzyme electrode was turned back to the foregoing preservation solution and then immersed in a measurement sample to carry out measurement. On completion of the measurement, the enzyme electrode part was washed and turned back to the preservation solution to be made ready for the next measurement.

Using the measurement apparatus, an actual urine sample containing 21 mg/dl glucose at 32° C. was measured at the ambient temperature, 10, 15, 20, 25, and 30° C. In order to prevent temperature decrease of the actual urine sample during the evaluation, the sample was put in a thermostat apparatus to be evaluated.

Comparative Example 3

As a reference experiment of the example 3, using a measurement apparatus comprising a calibration liquid container provided with no temperature adjustment function, the same measurement was carried out. The temperature of the calibration liquid was constantly kept at same as the ambient temperature or extremely close to the ambient temperature.

Figure 21:
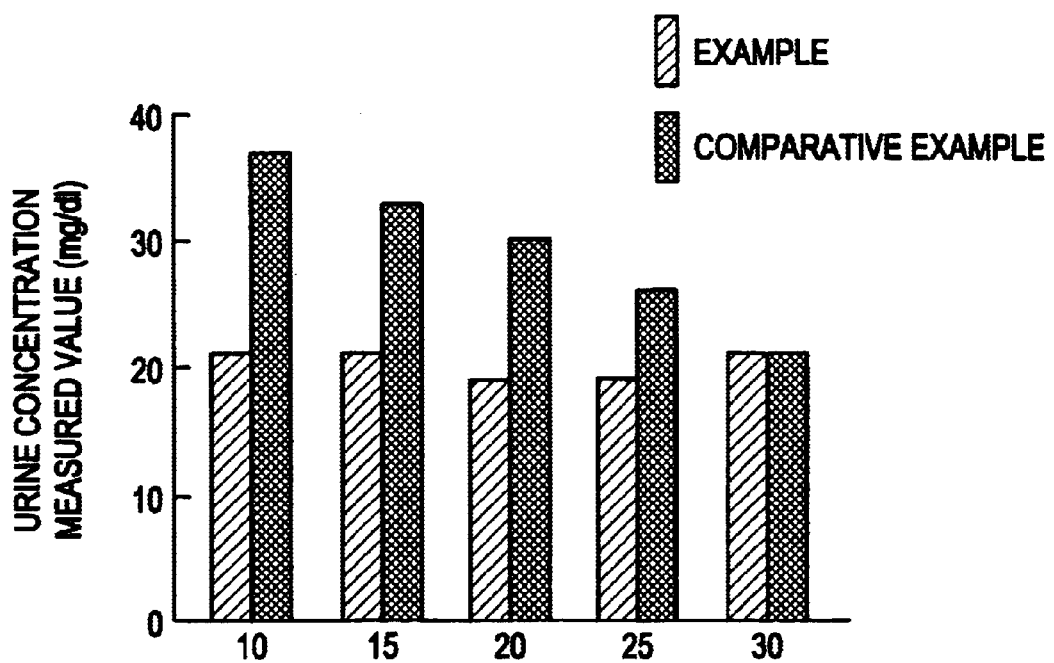
FIG. 21 is a graph showing the urine sugar measurement results using a measurement apparatus according to the present invention.

The measurement results of the example 3 and the comparative example 3 were shown in FIG. 21. The measurement by the measurement apparatus of the example 3 showed 21 mg/dl without being affected by the ambient temperature, whereas the measurement values were higher as the ambient temperature was lower showing that the measurement was easy to be affected by the temperature. The cause of that was because the calibration liquid was affected with the ambient temperature and calibration of the apparatus could not normally be carried out. According to the foregoing finding, it was made clear that the measurement at a high precision can be performed by installing a temperature adjustment function in the calibration liquid container.

Example 4

In the above-described embodiments, the measurement apparatuses were made to be a cartridge type and portable measurement apparatus, however the measurement apparatus may be a fixed type measurement apparatus. In the present example, the measurement apparatus comprising a urine sugar sensor was installed in a toilet stool in a toilet.

At first, a working electrode (surface area of 7 mm²) made of platinum, a counter electrode (surface area of 4 mm²) and two reference electrodes (surface area of 1 mm²) of silver/silver chloride were formed on a quartz substrate of 10 mm×6 mm size. Continuously, after a bonding layer was formed by spin coating using a 1 v/v% γ-aminopropyltriethoxysilane solution, a fixed enzyme layer was formed by spin coating using a 22.5 w/v% albumin solution containing glucose oxidase and 1 v/v% glutaraldehyde to form a fixed enzyme electrode layer. On the entire surface of the fixed enzyme electrode layer was spin-coated with a solution of poly (1H, 1H-perfluorooctyl methacrylate) (the number average molecular weight about 7000) adjusted to be 0.3% by mass using perfluorohexane and then dried to form a limited permeation layer. As described above, an electric current detection type urine sugar sensor was manufactured. The schematic structure of the urine sugar sensor was same as shown in FIG. 17.

Figure 19:
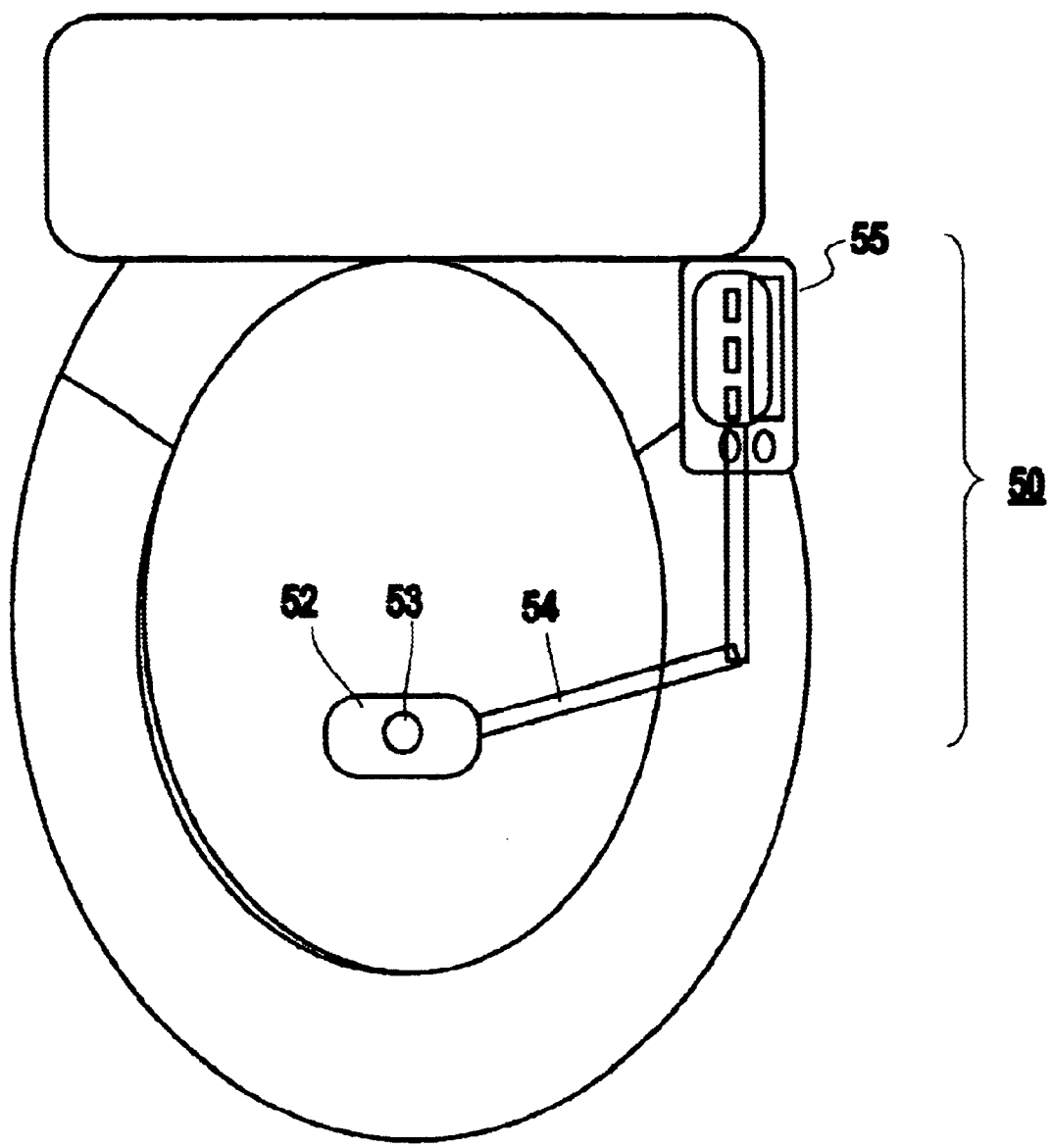
FIG. 19 is a schematic view of a measurement apparatus according to the present invention.

The urine sugar sensor 53 obtained in the above-described manner was disposed as shown in FIG. 19. The urine sugar sensor 53 was installed integrally with a urine collector 52 and supported by a supporting part 54. The output of the urine sugar sensor 53 was led to a measurement and display part 55 and the measurement results were displayed.

Figure 20:
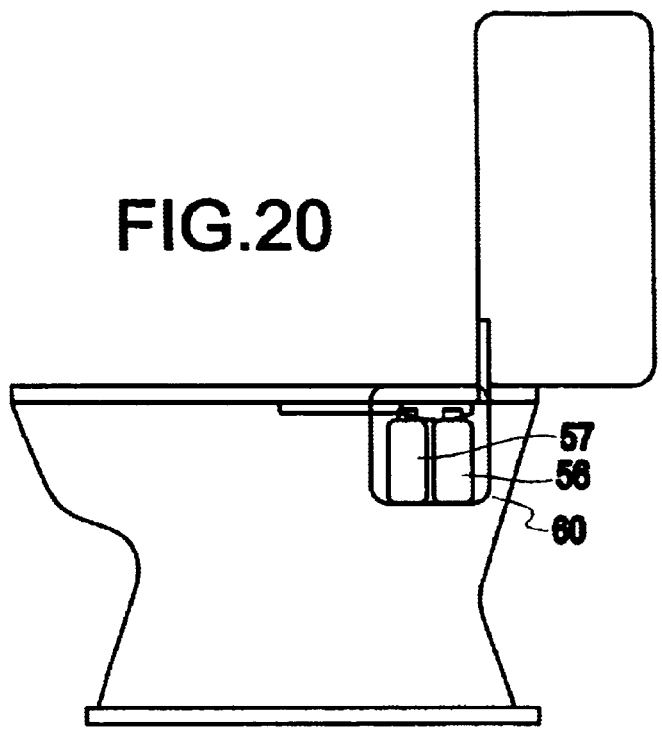
FIG. 20 is a schematic view of a measurement apparatus according to the present invention.

In the lower part of the measurement and display part 55, as shown in FIG. 20, a storage part 60 was installed and a calibration liquid container 56, a preservation liquid and washing liquid container 57 were housed in the inside. The size of the storage part was about 100 mm in depth and 100 mm in height. The liquid container 56 had the same structure as the container shown in FIG. 22 and was equipped with a temperature control part comprising a heater and a thermostat.

Figure 18:
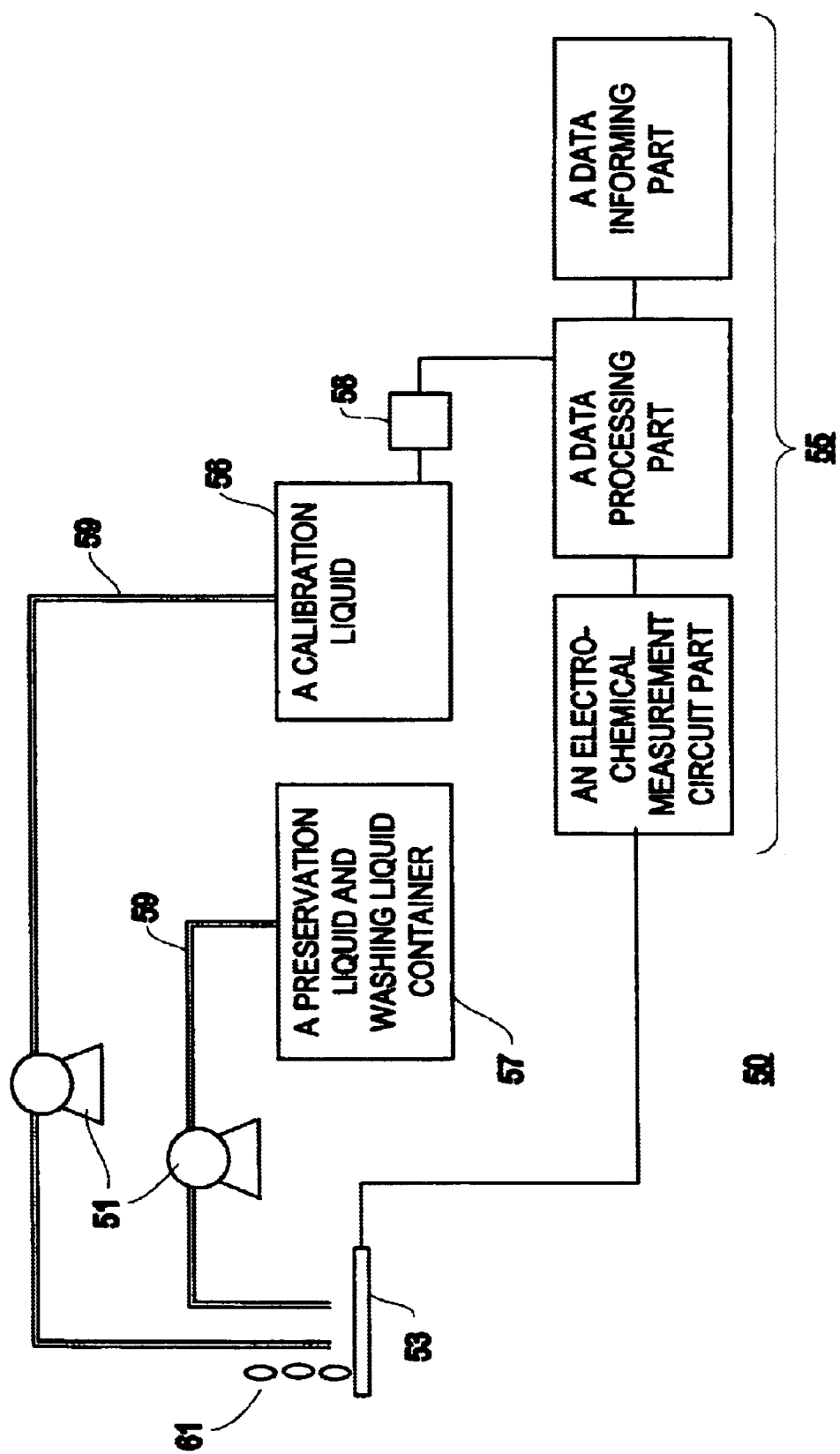
FIG. 18 is a schematic diagram showing a measurement apparatus according to the present invention.

The constitution of the entire measurement apparatus 50 was as shown in FIG. 18. A calibration liquid, a preservation liquid, and a washing liquid stored in the calibration liquid container 56 and the preservation liquid and washing liquid container 57 were made possible to be led to the surface of the urine sugar sensor 53 respectively through the pipeline 59 and a pump 51. Measurement was carried out by directly bringing urine 61 into contact with the surface of the urine sugar sensor 53 and data processing the output of the urine sugar sensor 53. The data processing was carried out by the measurement and display part 55 composed of an electrochemical measurement circuit part, a data processing part, and a data display part. The data processing part was connected with a temperature sensor 58 attached to the calibration liquid container 56 and the computed value correction was to be performed depending on the temperature of the calibration liquid. Incidentally, since the measurement apparatus of the present example was provided with the limited permeation layer, urine was made to be subjected to the measurement as a raw liquid as it was.

Next, description will be given regarding the measurement method using the foregoing measurement apparatus below.

At first, the electric power switch of the calibration liquid container was turned on and the temperature of the temperature adjustment switch was set at the same value, 32° C., as that of a measurement sample. Next, a washing liquid, which was a buffer solution of a TES [N-tris(hydroxymethyl)-methyl-2-aminoethanesulfonic acid] at pH 7 containing 150 mM sodium chloride was jetted toward the enzyme electrode part of the urine sugar sensor. After it was confirmed that the calibration liquid was at the set temperature, the calibration liquid was jetted toward the enzyme electrode and under such a situation, the calibration switch was pushed down to carry out calibration of the urine sugar sensor. Then, after the calibration liquid on the enzyme electrode surface was washed out again with the washing liquid, urine was showered to the enzyme electrode part to carry out measurement. On completion of the measurement, the enzyme electrode part was washed with the washing liquid.

As described in the present example, in the case of carrying out the measurement in a manner that the sample (urine) was directly splashed to the sensor part, the measurement error owing to the detection delay of the temperature of the calibration liquid became significant. Since the apparatus of the present example was provided with a temperature control means which was installed in the calibration liquid, in place of the thermometer installed in the biosensor part in a conventional manner, highly precise calibration was made possible and even if the urine sugar level was low, measurement results with stable and high repeat accuracy were obtained.

What is claimed is:

1. A measurement apparatus, comprising:

a main body comprising a biosensor for carrying out measurement of a specified component in a liquid sample using an enzymatic reaction, and a computation processing part for obtaining a computed value by computing an output signal of the biosensor; and a container, separately provided from said main body, for storing a calibration liquid for calibrating the biosensor, wherein the container comprises a temperature control means for keeping the calibration liquid at a constant temperature.

2. The measurement apparatus according to claim 1, wherein said biosensor comprises an enzyme layer for measuring the liquid sample.

3. The measurement apparatus according to claim 1, wherein the biosensor comprises an electrochemical sensor equipped with an enzyme electrode as a working electrode.

4. The measurement apparatus according to claim 3, wherein the liquid sample comprises urine.

5. A measurement apparatus, comprising:

a biosensor for carrying out measurement of a specified component in a liquid sample using an enzymatic reaction;

a computation processing part for obtaining a computed value by computing an output signal of the biosensor; and a container for storing a calibration liquid for calibrating the biosensor, wherein the container is equipped with temperature measurement means for measuring a temperature of the calibration liquid and the computation processing part has a function of correcting the computed value depending on the temperature of the calibration liquid measured by the temperature measurement means.

6. The measurement apparatus according to claim 5, wherein said biosensor comprises an enzyme layer for measuring the liquid sample.

7. The measurement apparatus according to claim 5, wherein the biosensor comprises an electrochemical sensor equipped with an enzyme electrode as a working electrode.

8. The measurement apparatus according to claim 7, wherein the liquid sample comprises urine.

* * * * *